United States Patent
Bilz et al.

(10) Patent No.: US 11,897,836 B2
(45) Date of Patent: Feb. 13, 2024

(54) PROCESS FOR THE PREPARATION OF METHIONINE

(71) Applicant: Evonik Operations GmbH, Essen (DE)

(72) Inventors: Jürgen Bilz, Freigericht (DE); Cornelia Borgmann, Frankfurt (DE); Achim Fischer, Goldbach (DE); Lucas Geist, Freigericht (DE); Anja Nordschild, Oberursel (DE); Christian Renner, Gruendau (DE); Christian Reus, Freigericht (DE); Axel Ronneburg, Hanau (DE)

(73) Assignee: Evonik Operations GmbH, Essen (DE)

( * ) Notice: Subject to any disclaimer, the term of this patent is extended or adjusted under 35 U.S.C. 154(b) by 116 days.

(21) Appl. No.: 17/618,145

(22) PCT Filed: Jun. 8, 2020

(86) PCT No.: PCT/EP2020/065758
§ 371 (c)(1),
(2) Date: Dec. 10, 2021

(87) PCT Pub. No.: WO2020/249495
PCT Pub. Date: Dec. 17, 2020

(65) Prior Publication Data
US 2022/0227706 A1    Jul. 21, 2022

(30) Foreign Application Priority Data
Jun. 13, 2019 (EP) .................................... 19179839

(51) Int. Cl.
*C07C 319/20* (2006.01)
(52) U.S. Cl.
CPC .................................. *C07C 319/20* (2013.01)
(58) Field of Classification Search
None
See application file for complete search history.

(56) References Cited

U.S. PATENT DOCUMENTS

| | | |
|---|---|---|
| 2017/0275247 A1 | 9/2017 | Matsumura |
| 2019/0077750 A1 | 3/2019 | Ikeguchi |

FOREIGN PATENT DOCUMENTS

| | | |
|---|---|---|
| EP | 3 199 519 A1 | 8/2017 |
| EP | 3 453 701 A1 | 3/2019 |

OTHER PUBLICATIONS

Baalousha ("Characterisation of structural and surface speciation of representative commercially available cerium oxide nanoparticles" Environ. Chem. 2010, 7, pp. 377-385) (Year: 2010).*
Luong ("Affinity Cross-Flow Filtration for Purifying Biomolecules" Nature Biotechnology, 1987, vol. 7, pp. 564-566) (Year: 1987).*
International Search Report and Written Opinion dated Aug. 13, 2020 in PCT/EP2020/065758 filed on Jun. 8, 2020, 13 pages.
Extended European Search Report dated Nov. 28, 2019 in European Patent Application No. 19179839.6, 7 pages.

* cited by examiner

*Primary Examiner* — Amy C Bonaparte
(74) *Attorney, Agent, or Firm* — Oblon, McClelland, Maier & Neustadt, L.L.P.

(57) ABSTRACT

The present invention relates to a process for the preparation of methionine comprising the step of contacting a solution or suspension comprising 2-amino-4-(methylthio)butanenitrile and/or 2-amino-4-(methylthio)butaneamide with water in the presence of a catalyst to give a methionine comprising mixture, wherein the catalyst comprises CeO2 comprising particles, wherein the CeO2 comprising particles have a BET surface area of from 175 to 300+/−10% m2/g measured according to DIN ISO 9277-5 (2003), a mean maximum Feret diameter $x_{Fmax}$, mean of from 3+/−10% to 40+/−10% nm and a mean minimum Feret diameter $x_{Fmin}$, mean of from 2+/−10% to 30+/−10% nm, both measured according to DIN ISO 9276-6 (2012).

13 Claims, No Drawings

PROCESS FOR THE PREPARATION OF METHIONINE

The present invention relates to a process for the preparation of methionine in one step using 2-amino-4-(methylthio)butanenitrile and/or 2-amino-4-(methylthio)butaneamide as starting material.

Methionine is an essential amino acid, which is of great importance as a feed supplement, in particular for poultry. The present standard industrial production of methionine starts from methyl mercaptan, acrolein and hydrogen cyanide. First, methyl mercaptan is added to the carbon carbon-double bond of acrolein in a Michael addition to give the intermediate 3-(methylthio)propionaldehyde. Next, this aldehyde is reacted with hydrogen cyanide to give 2-hydroxy-4-(methylthio)butanenitrile, which is further reacted with ammonia and carbon dioxide to the corresponding hydantoin derivate. Alternatively, the hydantoin derivative is also obtainable by reacting 3-(methylthio)propionaldehyde with hydrogen cyanide, ammonia and carbon dioxide. The basic hydrolysis of this hydantoin gives the alkali salt of methionine. Its neutralization with an acid, e.g. by addition of $H_2SO_4$ or by bubbling carbon dioxide trough an aqueous solution containing the alkali salt of methionine, gives racemic methionine.

Alternatively, it is also possible to prepare methionine by hydrolysis of 2-amino-4-(methylthio)butanenitrile or 2-amino-4-(methylthio)butaneamide. It is well accepted that the hydrolysis of 2-amino-4-(methylthio)butanenitrile, obtained either from the reaction of 2-hydroxy-4-(methylthio)butanenitrile with ammonia or from the reaction of 3-(methylthio)propionaldehyde with hydrogen cyanide and ammonia, proceeds via the intermediate 2-amino-4-(methylthio)butaneamide to give methionine as the desired product. First, the nitrile group of the 2-amino-4-(methylthio) butanenitrile is hydrolyzed to an amide group to give the 2-amino-4-(methylthio)butaneamide. Subsequently, the amide group of the 2-amino-4-(methylthio)butaneamide is hydrolyzed to a hydroxyl group to give methionine.

The published patent application JP S54-46717 discloses a method for the preparation of an amino acid by reacting an alpha-aminonitrile with water in the presence of zinc metal or zinc oxide. However, the yields for methionine are not satisfactory.

The published patent application JP H03-93757 discloses a method for hydrolyzing an alpha-aminonitrile to the corresponding alpha-amino acid in the presence of zirconium dioxide-based catalysts. However, the methionine yields are neither satisfactory nor consistent.

The U.S. Pat. No. 6,417,395 B1 discloses a catalyzed hydrolysis of 2-amino-4-(methylthio)butanenitrile to methionine. However, the catalyst systems used in this document do not show on optimum performance with respect to the formation of the desired product methionine. Rather, it appears that they strongly vary depending on the solvent used in the hydrolysis.

The published patent application EP 3199519 A1 discloses a method for producing methionine, by contacting 2-amino-4-(methylthio)butanenitrile and water with each other in the presence of an oxide catalyst containing cerium. Specifically, the catalyst used in this method is either cerium oxide, e.g. cerium(III) oxide ($Ce_2O_3$), cerium(IV) oxide ($CeO_2$), a mixture thereof, or cerium oxide compounds having these mixed phases, or an oxide solid solution containing cerium, e.g. $CeO_2$—$ZrO_2$ (ceria-zirconia), $CeO_2$—$Y_2O_3$, and $CeO_2$—$La_2O_3$. However, the yields for the thus obtained methionine are not consistent. Rather, the results strongly vary, depending on the type and the amount and source of the $CeO_2$-based catalyst used, and additional specific characteristics of the process. Even in the examples, in which methionine was produced in the presence of pure $CeO_2$, the yields for methionine strongly vary from 60% to 95%. Further, the examples of EP 3199519 A1 do not specify the other components in the thus obtained methionine comprising product mixture, in particular, whether the other components are unconverted starting compounds or by-products. Therefore, the experimental data of this document do not allow any conclusions if all types of $CeO_2$-based catalysts are really suitable for the catalyzed hydrolysis of 2-amino-4-(methylthio)butanenitrile.

Accordingly, there was a need for an improved process for preparing methionine in one step using 2-amino-4-(methylthio)butanenitrile and/or 2-amino-4-(methylthio)butaneamide as starting material.

It was found that this problem is solved by use of a catalyst comprising $CeO_2$ comprising particles, wherein the $CeO_2$ comprising particles have a BET surface area of from 175 to 300+/−10% $m^2/g$ measured according to DIN ISO 9277-5 (2003) in combination with a mean maximum Feret diameter $x_{Fmax, mean}$ of from 3+/−10% to 40+/−10% nm and a mean minimum Feret diameter $x_{Fmin, mean}$ of from 2+/−10% to 30+/−10% nm, both measured according to DIN ISO 9276-6 (2012). Specifically, it was found that one of these parameters is not sufficient to characterize the catalysts, which give the desired conversion rates and selectivities. Rather, it needs a catalyst with a combination of the specific parameters in the given ranges to obtain the desired conversion rates and selectivities in the preparation of methionine using 2-amino-4-(methylthio)butanenitrile and/or 2-amino-4-(methylthio)butaneamide as starting compound.

Object of the present invention is therefore a process for the preparation of methionine comprising the step of contacting a solution or suspension comprising 2-amino-4-(methylthio)butanenitrile and/or 2-amino-4-(methylthio)butaneamide with water in the presence of a catalyst to give a methionine comprising mixture, wherein the catalyst comprises $CeO_2$ comprising particles, wherein the $CeO_2$ comprising particles have a BET surface area of from 175 to 300+/−10% $m^2/g$ measured according to DIN ISO 9277-5 (2003), a mean maximum Feret diameter $x_{Fmax, mean}$ of from 3+/−10% to 40+/−10% nm and a mean minimum Feret diameter $x_{Fmin, mean}$ of from 2+/−10% to 30+/−10% nm, both measured according to DIN ISO 9276-6 (2012).

In the context of the present invention the terms maximum Feret diameter and minimum Feret diameter are used as known from the industrial standard DIN ISO 9276-6 (2012). They are macro shape descriptors, which reflect the geometric proportions of a particle, such as a crystal or a particle with a certain degree of crystallinity. In this respect, they denote the distance between two parallel tangents applied to a particle. Specifically, the maximum Feret diameter corresponds to the "length" of the particle, and the minimum Feret diameter corresponds to the "width" of the particle, to which the tangents were applied.

In the context of the present invention the term mean is used to denote the arithmetic mean, also called the mathematical expectation or average, of the parameter in question. It is the central value of a discrete set of measured values for the parameter, specifically, the sum of the measured values for the parameter divided by the number of measurements.

In the context of the present invention the term methionine comprising mixture denotes a mixture containing the catalyst, where appropriate, unconverted starting compounds, i.e. 2-amino-4-(methylthio)butanenitrile and/or 2-amino-4-(methylthio)butaneamide, and methionine in pure form, and/or in admixture with ammonia, released during the contacting step, as ammonium methioninate. After a separation of the catalyst from the methionine comprising mixture, said term denotes a mixture comprising, where appropriate, unconverted starting compounds, i.e. 2-amino-4-(methylthio)butanenitrile and/or 2-amino-4-(methylthio)butaneamide, and methionine in pure form, and/or in admixture with ammonia, released during the contacting step, as ammonium methioninate.

In the context of the present invention the term+/−10% following explicitly mentioned values denotes deviations in the range of from −10% to +10% of the explicitly mentioned values and thus includes all values in this range. The term+/−10% also expresses that deviations from any explicitly mentioned values with or without the additional 10 range are also encompassed by the scope of the claimed invention, provided that said deviations also lead to the effects of the claimed invention.

The process according to the present invention, and specifically, the use of the catalysts comprising $CeO_2$ comprising particles according to the present invention catalyze the hydrolysis of 2-amino-4-(methylthio)butanenitrile and/or 2-amino-4-(methylthio)butaneamide to a mixture comprising 2-amino-4-(methylthio)butaneamide and methionine or to methionine each with a higher selectivity than the catalysts of EP 3199519 A1.

In principle, the process according to the present invention is not subject to any limitations regarding the content of $CeO_2$ in the catalyst used. Therefore, the catalyst can comprise from 25 to 100 wt.-% of $CeO_2$. Every catalyzed reaction is typically accompanied by a certain loss of the catalyst, which is also referred to as catalyst leaching. Depending on the price of the catalytically active component in the catalyst, the catalyst loss or leaching has an impact on the economy of the process to greater or lesser extent. Industrially, it is therefore beneficial to use the catalyst in a catalyzed reaction in an amount as small as possible. For example, the catalyst with the $CeO_2$ comprising particles is mixed with a further component, which considered as such is not catalytically active in the process according to the present invention. A suitable component in this respect is for example $ZrO_2$. It was found that the process according to the present invention already gives a methionine yield of 95% when the specific catalyst comprises only 25 wt.-% of $CeO_2$, for example with a catalyst comprising particles of $CeO_2$, which has been mixed with three equivalents of $ZrO_2$ per one equivalent of $CeO_2$.

In an embodiment of the process according to the present invention the catalyst comprises from 25 to 100 wt.-% of $CeO_2$, based on the total weight of the catalyst.

Notwithstanding, it is preferred that the catalyst according to the present invention contains more than 25 wt.-% of the $CeO_2$, based on the total weight of the catalyst, in order to obtain the highest possible conversion rates and methionine yields within a rather short time. Therefore, the catalyst according to the present invention preferably comprises from 25 to 100 wt.-%, from 30 to 100 wt.-%, from 35 to 100 wt.-%, from 40 to 100 wt.-%, from 45 to 100 wt.-%, from 50 to 100 wt.-%, from 55 to 100 wt.-%, from 60 to 100 wt.-%, from 65 to 100 wt.-%, from 70 to 100 wt.-%, from 75 to 100 wt.-%, from 80 to 100 wt.-%, from 85 to 100 wt.-%, from 90 to 100 wt.-%, or from 95 to 100 wt.-% of $CeO_2$, each based on the total weight of the catalyst.

Like the catalyst as a whole, also the $CeO_2$ comprising particles are not limited with respect to a specific $CeO_2$ content. Specifically, it was found that even $CeO_2$ comprising particles with varying contents of $CeO_2$ give comparable results in the process according to the present invention. In particular, $CeO_2$ comprising particles with from 50 to 100 wt.-% of $CeO_2$ and the remainder being one or more metals or metal oxides different from cerium or cerium oxides, such as $ZrO_2$, give particularly good results in the process according to the present invention. Catalysts suitable for the process according to the present invention therefore, comprise particles comprising $CeO_2$, $(CeO_2)_{0.5}$—$(ZrO_2)_{0.5}$, $(CeO_2)_{0.7}$—$(ZrO_2)_{0.3}$, and/or $(CeO_2)_{0.8}$—$(ZrO_2)_{0.2}$, or pure $CeO_2$.

In one embodiment of the process according to the present invention the $CeO_2$ comprising particles comprise from 50 to 100 wt.-% of $CeO_2$.

Specifically, the $CeO_2$ comprising particles comprise 50 wt.-%, 70 wt.-%, 80 wt.-% or 100 wt.-% of $CeO_2$.

Experiments have shown that catalysts according to the present invention, where the $CeO_2$ comprising particles have a BET surface area in the range of 200 to 280 $m^2/g$ give a methionine with a selectivity of up to 100% and a sum selectivity for the formation of methionine and 2-amino-4-(methylthio)butaneamide of up to 100% in the catalyzed hydrolysis of 2-amino-4-(methylthio)-butanentrile (T=75° C., t=120 min., 4 g catalyst (0.35 eq.) and 10 g 2-amino-4-(methylthio)-butanentrile).

In one embodiment of the process according to the present invention the $CeO_2$ comprising particles have a BET surface of from 200+/−10% to 280+/−10% $m^2/g$, measured according to DIN ISO 9277-5 (2003). In a further preferred embodiment the $CeO_2$ comprising particles have a BET surface of from 225+/−10% to 265+/−10% $m^2/g$, measured according to DIN ISO 9277-5 (2003).

It was also found that the catalysts according to the present invention, which comprise rather compact $CeO_2$ comprising particles are more beneficial for a high methionine yield and a high methionine selectivity than catalysts comprising sphere-like $CeO_2$ comprising particles. A suitable parameter for distinguishing the sphere-like $CeO_2$ comprising particles from compact $CeO_2$ comprising particles is the so-called aspect ratio. This parameter describes the ratio of the sides of a particle; specifically, it describes the ratio of the minimum Feret diameter to maximum Feret diameter, $x_{Fmin}/x_{Fmax}$, according to DIN ISO 9276-6 (2012). In the context of the present invention it is preferred to use the mean aspect ratio because the $CeO_2$ comprising particles are already described by the mean minimum Feret diameter $x_{Fmin,\ mean}$ and the mean maximum Feret diameter $x_{Fmax,\ mean}$. The mean aspect ratio can therefore be expressed as $x_{Fmin,\ mean}/x_{Fmax,\ mean}$. Sphere-like particles have similar Feret diameters and therefore have a (mean) aspect ratio very close to 1. A perfectly spherical particle has a (mean) aspect ratio of 1. By comparison, the $CeO_2$ comprising particles of the catalysts used in the process according to the present invention have a mean aspect ratio of less than 1 and therefore, Feret diameters which are not identical.

In another embodiment of the process according to the present invention, the mean minimum Feret diameter of the $CeO_2$ comprising particles is always smaller than the mean maximum Feret diameter of said particles.

Preferably, the $CeO_2$ comprising particles have a mean minimum Feret diameter $x_{Fmin,\ mean}$ ranging from 3+/−10% to 10+/−10% nm. It is further preferred, that the $CeO_2$ comprising particles have a mean maximum Feret diameter $x_{Fmax,\ mean}$ ranging from 4+/−10% to 10+/−10% nm. In particular, the $CeO_2$ comprising particles have a mean minimum Feret diameter $x_{Fmin,\ mean}$ ranging from 3+/−10% to 10+/−10% nm and a mean maximum Feret diameter $x_{Fmax,\,mean}$ ranging from 4+/−10% to 10+/−10% nm.

In an embodiment of the process according to the present invention the $CeO_2$ comprising particles have a BET surface area of from 175 to 300+/−10% $m^2/g$, measured according to DIN ISO 9277-5 (2003), a mean minimum Feret diameter $x_{Fmin,\,mean}$ ranging from 3+/−10% to 10+/−10% nm, and a mean maximum Feret diameter $x_{Fmax,\,mean}$ ranging from 4+/−10% to 10+/−10% nm, both measured according to DIN ISO 9276-6 (2012).

In a preferred embodiment of the process according to the present invention the $CeO_2$ comprising particles have a BET surface area of from 225+/−10% to 265+/−10% $m^2/g$, measured according to DIN ISO 9277-5 (2003), a mean minimum Feret diameter $x_{Fmin,\,mean}$ ranging from 3+/−10% to 10+/−10% nm, and a mean maximum Feret diameter $x_{Fmax,\,mean}$ ranging from 4+/−10% to 10+/−10% nm, both measured according to DIN ISO 9276-6 (2012).

It was found that $CeO_2$ comprising particles with a mean aspect ratio greater than 0.75, measured according to DIN ISO 9276-6 (2012), give lower methionine yields and lower methionine selectivity than rather compact $CeO_2$ comprising particles. Specifically, it was found that catalysts comprising $CeO_2$ comprising particles with a mean aspect ratio of from 0.55+/−10% to 0.80+/−10%, in particular from 0.6+/−10% to 0.8+/−10% give particularly high methionine yields and high methionine selectivity.

In yet another embodiment of the process according to the present invention, the $CeO_2$ comprising particles have a mean aspect ratio $x_{Fmin,\,mean}/x_{Fmax,\,mean}$ of from 0.55+/−10% to 0.80+/−10%, measured according to DIN ISO 9276-6 (2012).

According to the present invention the catalyst comprises $CeO_2$ comprising particles, wherein the $CeO_2$ comprising particles have a BET surface area of from 175 to 300+/−10% $m^2/g$ measured according to DIN ISO 9277-5 (2003), a mean maximum Feret diameter $x_{Fmax,\,mean}$ of from 3+/−10% to 40+/−10% nm and a mean minimum Feret diameter $x_{Fmin,\,mean}$ of from 2+/−10% to 30+/−10% nm, both measured according to DIN ISO 9276-6 (2012). From the definition of the Feret diameters, it follows that their values can strongly vary. Further, Feret diameters are not diameters in the strictest sense but rather reflect the geometric proportions of a particle, such as a crystal or a particle with a certain degree of crystallinity. Therefore, it is not possible to describe the size of primary particles based alone on the Feret diameters. The so-called equivalent circular diameter $x_A$ is a suitable measure for describing the primary particle sizes of the $CeO_2$ comprising particles in the catalysts according to the present invention. In the context of the present invention the term equivalent circular diameter is used as known from the industrial standard DIN ISO 9276-6 (2012). In general, the equivalent circular diameter corresponds to the diameter of a circle with the same projected area as the particle in question. The equivalent circular diameter is calculated using the following formula $$x_A = \sqrt{\frac{4 \times A}{\pi}}$$

with A being the projection area of the particle in question, given in $nm^2$ and measured according to DIN ISO 9276-6 (2012). Typically, the projected area of the particles in question is obtained by means of image analysis software in the graphical analysis of high-resolution transmission electron microscopy (HR-TEM) images of a meaningful number (at least 100, preferably at least 200, 300, 400 or 500) of particles. In the context of the present invention the mean equivalent circular diameter $x_A$ is used, which allows to describe the general mean primary particle size for the whole number of analyzed $CeO_2$ comprising particles. The $CeO_2$ comprising particles in the catalyst of the present invention are characterized by a mean equivalent circular diameter $x_A$ of from 3+/−10% to 30+/−10% nm, preferably of from 4+/−10% to 30+/−10%, from 10+/−10% to 30+/−10% nm or from 4+/−10% to 20+/−10%, measured according to DIN ISO 9276-6 (2012). By comparison, the $CeO_2$ comprising particles in the catalyst #4 (purchased from Wako, cf. table 1 in the experimental section) have an equivalent circular diameter of ca. 48 nm and are thus larger and bulkier than the catalysts according to the present invention.

In one embodiment of the process according to the present invention the $CeO_2$ comprising particles have a mean equivalent circular diameter $x_{A,\,mean}$ of from 3+/−10% to 30+/−10% nm, measured according to DIN ISO 9276-6 (2012).

A further analysis of the catalysts for the process according to the invention showed that a lattice plane distance of from 0.24+/−10% to 0.32+/−10% nm, preferably 0.28+/−10% to 0.32+/−10% nm, in the $CeO_2$ comprising particles is beneficial for high methionine yields and a high methionine selectivity.

In a further embodiment of the process according to the present invention, the $CeO_2$ comprising particles have a lattice plane distance of from 0.24+/−10% to 0.32+/−10% nm.

Particles with a lattice plane distance of from 0.24+/−10% to 0.32 nm+/−10% have a (111) surface, which is a requirement for the presence of octahedral particles. This finding is in accordance with the HR-TEM picture of very efficient and selective catalysts in the process according to the present invention, which comprise octahedral $CeO_2$ comprising particles. The catalysts comprising the $CeO_2$ comprising particles according to the present invention, which have a lattice plane distance of from 0.24+/−10% to 0.32+/−10% nm, catalyze the hydrolysis of 2-amino-4-(methylthio)butanenitrile to methionine with a yield of at least 99%. By comparison, a catalyst comprising $CeO_2$ comprising particles not according to the invention with a lattice plane distance of 0.40 nm (see comparative catalyst #3 in example 3.3) gives a methionine yield of only 35%. Indeed, the closer the $CeO_2$ comprising particles come to a mean aspect ratio of 0.71, the closer they come to an octahedral shape. A perfect octahedral particle has an aspect ratio of 0.71. Therefore, the presence of octahedral $CeO_2$ comprising particles is also in accordance with the fact that the efficient catalysts comprise $CeO_2$ comprising particles with a mean aspect ratio of from 0.55+/−10% to 0.80+/−10%, in particular from 0.6+/−10% to 0.8+/−10%.

In yet a further embodiment of the process according to the present invention, the $CeO_2$ comprising particles comprise octahedral particles.

It was found that catalysts containing $CeO_2$ comprising particles, which are spherical and have rather soft edges, give a low yield and selectivity for the formation of methionine. By comparison, effective catalysts in the process according to the present invention contain $CeO_2$ comprising particles with a rather crystalline appearance, i.e. with a crystallinity of at least 50%. Specifically, the effective catalysts can be distinguished by the clear and identifiable geometrical appearance with clear edges, corners and areas of their CeO$_2$ comprising particles from the less effective catalysts. In comparison, the less effective catalysts have CeO$_2$ comprising particles with rounded or smooth corners and edges, which cannot be clearly assigned to a specific geometric appearance.

In another embodiment of the process according to the present invention the CeO$_2$ comprising particles have a crystallinity of at least 50%.

Preferably, the CeO$_2$ comprising particles have a crystallinity of from 50 to 100%, of from 50 to 95%, or of from 55 to 90%.

In principle, the process according to the present invention is not limited regarding the temperature at which the contacting step is performed. Therefore, the contacting step can be performed at any temperature at which the starting compound 2-amino-4-(methylthio)butanenitrile is thermically stable. Specifically, no by-products were detected in the methionine comprising mixture obtained from the hydrolysis of 2-amino-4-(methylthio)butanenitrile and/or 2-amino-4-(methylthio)butaneamide in the process according to the present invention at a temperature of 90° C. at the most. For example, the contacting step can be performed at a temperature of from 20 to 90° C., of from 30 to 90° C., of from 40 to 90° C., of from 50 to 90° C., of from 60 to 90° C., of from 70 to 90° C. or of from 80 to 90° C. For example, the process according to the present invention already gives full conversion of the starting material 2-amino-4-(methylthio)butanenitrile and a methionine yield between 99 and 100% at a relatively low temperature of 75° C. and a reaction time of 2 hours with 4 g (0.35 equivalents) of catalysts and 10 g of the starting compound. By comparison, 4% methionine sulfoxide, i.e. oxidized methionine as undesired by-product, is formed when the hydrolysis of 2-amino-4-(methylthio)butanenitrile to methionine is performed at a temperature of 105° C.

In one embodiment the contacting step of the process according to the present invention is performed at a temperature of 90° C. at the most, with a 2-amino-4-(methylthio)butanenitrile comprising solution or suspension. Preferably, the contacting step of the process according to the present invention is performed at a temperature of from 50 to 90° C., with a 2-amino-4-(methylthio)butanenitrile comprising solution or suspension.

The process according to the present invention aims at achieving the highest possible yield for methionine. However, there may be cases in which the starting material, in particular the 2-amino-4-(methylthio)butanenitrile is not completely converted to methionine or not to the desired degree.

Here, the remainder is in particular 2-amino-4-(methylthio)butaneamide. Since said 2-amino-4-(methylthio)butaneamide is an intermediate and a suitable starting material in the process according to the present invention, the methionine comprising mixture from a (first) contacting step is preferably fed to a further contacting step of the process according to the present invention. Here, the 2-amino-4-(methylthio)butaneamide containing solution or suspension is contacted with water in the presence of the specific catalyst according to the present invention to maximize the conversion to methionine.

In one embodiment of the process according to the present invention the methionine comprising mixture obtained from a contacting step is fed to at least one further contacting step.

The process according to the present invention therefore preferably comprises the steps of i) a first contacting of a solution or suspension comprising 2-amino-4-(methylthio)butanenitrile and/or 2-amino-4-(methylthio)butaneamide with water in the presence of a catalyst to give a methionine comprising mixture, wherein the catalyst comprises CeO$_2$ comprising particles, wherein the CeO$_2$ comprising particles have a BET surface area of from 175 to 300+/−10% m$^2$/g, preferably 200+/−10% to 280+/−10% m$^2$/g, or 225+/−10% to 265+/−10% m$^2$/g, measured according to DIN ISO 9277-5 (2003), a mean maximum Feret diameter $x_{Fmax,\ mean}$ of from 3+/−10% to 40+/−10% nm, preferably 4+/−10% to 10+/−10% nm and a mean minimum Feret diameter $x_{Fmin,\ mean}$ of from 2+/−10% to 30+/−10% nm, preferably 3+/−10% nm to 10+/−10% nm, both measured according to DIN ISO 9276-6 (2012), and ii) feeding the methionine comprising mixture obtained from step i) to at least one further contacting step.

In order to achieve a full conversion of the non-converted part of the starting compounds, it is preferred to perform a second or further contacting step at an elevated temperature, relative to the temperature in the first contacting step. Compared to a preceding contacting step, i.e. first contacting step, the elevated temperature, relative to the temperature in the preceding, i.e. first, contacting step does not lead to the quantifiable formation of any by-products. Therefore, the second or further contacting step can be performed at a temperature of more than 90° C. For example, the second or further contacting step can be performed at a temperature of from 70 to 140° C., of from 80 to 130° C., of from 90 to 120° C., or of from 100 to 110° C.

In another embodiment of the process according to the present invention, the at least one further contacting step is performed at a temperature ranging from 70 to 140° C.

The process according to the present invention can be conducted with a solution or suspension comprising 2-amino-4-(methylthio)butanenitrile and/or 2-amino-4-(methylthio)butaneamide in a concentration range preferably of from 1 to 30 wt.-%, of from 3 to 25 wt.-%, of from 6 to 24 wt.-%, or of from 6 to 20 wt.-%.

In one embodiment of the process according to the present invention the contacting step is performed with a solution or suspension comprising 2-amino-4-(methylthio)butanenitrile and/or 2-amino-4-(methylthio)butaneamide in a concentration range of from 1 to 30 wt.-%.

The process according to the present invention is not limited with respect to a specific shape or size of the catalysts comprising the CeO$_2$ comprising particles. In the simplest case, the catalyst is the powder obtained from the production of the CeO$_2$ comprising particles. However, when a catalyst consisting of fine particles is used in a catalyzed reaction, it is necessary to separate the fine powdery catalyst and the methionine comprising mixture from one another. A suitable separation step in the context of the present invention must meet the requirements of being efficient and applicable in a continuous process. The most common technique for separating particles from a liquid medium is the so-called dead-end filtration. However, this type of filtration is neither suitable for use in a completely continuous process nor for separating particles with a diameter of less than 10 μm from a liquid medium in large-scale applications. It was found that this problem is solved by using a continuous cross flow filtration. The cross-flow filtration, also known as tangential flow filtration, is a filtration technique in which the starting methionine and CeO$_2$ comprising suspension passes tangentially along the surface of the filter. A pressure difference across the filter drives components that are smaller than the pores through the filter (permeate). Components larger than the filter pores are retained and pass along the membrane surface, flowing back to the feed reservoir (retentate).

In a further embodiment the process according to the present invention further comprises the step of separating the catalyst from the methionine comprising mixture obtained in step i) and/or ii) by a continuous cross flow filtration.

The process according to the present invention therefore preferably comprises the steps of
i) a first contacting of a solution or suspension comprising 2-amino-4-(methylthio)butanenitrile and/or 2-amino-4-(methylthio)butaneamide with water in the presence of a catalyst to give a methionine comprising mixture, wherein the catalyst comprises $CeO_2$ comprising particles, wherein the $CeO_2$ comprising particles have a BET surface area of from 175 to 300+/−10% $m^2/g$, preferably 200+/−10% to 280+/−10% $m^2/g$, or 225+/−10% to 265+/−10% $m^2/g$, measured according to DIN ISO 9277-5 (2003), a mean maximum Feret diameter $x_{Fmax,\ mean}$ of from 3+/−10% to 40+/−10% nm, preferably 4+/−10% to 10+/−10% nm, and a mean minimum Feret diameter $x_{Fmin,\ mean}$ of from 2+/−10% to 30+/−10% nm, preferably 3+/−10% to 10+/−10% nm, both measured according to DIN ISO 9276-6 (2012),
ii) optionally, feeding the methionine comprising mixture obtained from step i) to at least one further contacting step, and
iii) separating the catalyst from the methionine comprising mixture of step i) and/or step ii) by a continuous cross flow filtration.

In alternative or in addition, the process according to the present invention therefore preferably comprises the steps of
i) a first contacting of a solution or suspension comprising 2-amino-4-(methylthio)butanenitrile and/or 2-amino-4-(methylthio)butaneamide with water in the presence of a catalyst to give a methionine comprising mixture, wherein the catalyst comprises $CeO_2$ comprising particles, wherein the $CeO_2$ comprising particles have a BET surface area of from 175 to 300+/−10% $m^2/g$, preferably 200+/−10% to 280+/−10% $m^2/g$, or 225+/−10% to 265+/−10% $m^2/g$, measured according to DIN ISO 9277-5 (2003), a mean maximum Feret diameter $x_{Fmax,\ mean}$ of from 3+/−10% to 40+/−10% nm, preferably 4+/−10% to 10+/−10% nm, and a mean minimum Feret diameter $x_{Fmin,\ mean}$ of from 2+/−10% to 30+/−10% nm, preferably 3+/−10% to 10+/−10% nm, both measured according to DIN ISO 9276-6 (2012),
ii) optionally, feeding the methionine comprising mixture obtained from step i) to at least one further contacting step,
iii) separating the catalyst from the methionine comprising mixture of step i) and/or step ii) by a continuous cross flow filtration, and
ii') optionally, repeating steps i) and iii), or steps i) to iii).

In principle, a polymeric or a ceramic membrane can be used for the separation of the $CeO_2$ comprising particles. However, the small $CeO_2$ comprising particles are abrasive when they are flowing across the membrane. Ceramic membranes made of but not limited to, for example, $TiO_2$, $ZrO_2$ or $Al_2O_3$ and supported on but not limited to, for example, $TiO_2$, $ZrO_2$ or $Al_2O_3$ proved to be resistant to abrasive $CeO_2$ comprising particles and are therefore preferred in a cross-flow filtration for separating the catalysts comprising the $CeO_2$ comprising particles from the methionine comprising mixture. When the catalyst of the process according to the present invention consists of the $CeO_2$ comprising particles as such, e.g. in the form of a fine powder, the catalyst particles, like the $CeO_2$ comprising particles, have an equivalent circular diameter $x_A$ of from 10 to 30 nm.

Therefore, the pore diameter of the membrane employed in the cross-flow filtration must be adequately chosen, in order to hold the catalyst particles back. At the same time the membrane used in the filtration must allow for a permeation of the methionine formed in the reaction through the membrane. The nominal molecular weight cutoff (NMWC), which is the molecular weight of the largest molecule that can pass through the membrane, is a suitable parameter for characterizing this feature of the membrane ranging of from 1 to 150 kD (kiloDalton=1000 g/mol), with 150 kD roughly corresponding to a pore diameter of ca. 20 nm. Thus, these ultrafiltration membranes with NWMC values from 1 to 150 kD can be used for efficiently separating the $CeO_2$ comprising particles in the retentate from the methionine comprising product solution in the permeate. The filtration with membrane pore sizes of less than 100 nm is also known as ultrafiltration, and the filtration with membrane pore sizes of 100 nm or more is also known as microfiltration. In the context of the present invention, microfiltration membranes with pore sizes of 100 nm up to 1 μm can be employed as well due to the formation of aggregates and agglomerates of the $CeO_2$ comprising catalyst particles resulting in effectively larger diameters for the aggregates and agglomerates of more than 100 nm up to several μm in diameter. However, microfiltration membranes do not retain all of the $CeO_2$ comprising catalyst particles as efficiently as an ultrafiltration membrane. In that case, a second filtration has to be performed with the permeate of the first filtration. It is therefore preferred that the continuous cross flow filtration is an ultrafiltration. It is further preferred that the continuous cross flow filtration is performed with a membrane, preferably a ceramic membrane, with a nominal molecular weight cutoff of from 1 to 150 kD and/or with a pore diameter of from 20 to 50 nm.

The desired product methionine can be separated from the thus obtained permeate solution, for example by crystallization or re-crystallization. The retentate solution or suspension containing the catalyst comprising $CeO_2$ particles, can be fed back, as described above, to a second or any further contacting step. For example, said retentate can be fed either back to the first reactor or to a downstream reactor, for performing a further contacting step. In case the retentate is fed to a downstream reactor, said downstream reactor is also equipped with a membrane, as described above, for separating the catalyst from the product solution.

Independently, whether the process according to the present invention starts from 2-amino-4-(methylthio)butaneamide or 2-amino-4-(methylthio)butanenitrile, it is always accompanied by the release of ammonia. In the first step of the hydrolysis of 2-amino-4-(methylthio)butanenitrile the cyanide group is converted to an amide group, which is in principle an addition of water to the carbon nitrogen triple bond of the cyanide group. Next, in the hydrolysis of the thus obtained 2-amino-4-(methylthio)butaneamide, the amide group is converted to the corresponding carboxylic acid group under release of ammonia. Thus, the hydrolysis of one equivalent of 2-amino-4-(methylthio)-butanenitrile and/or 2-amino-4-(methylthio)butaneamide is always accompanied by the release of one equivalent ammonia. In addition, the starting material 2-amino-4-(methylthio)butanenitrile already contains ammonia, in particular when it is prepared according to US 2012/215021 A1 by reacting 3-(methylthio)propionaldehyde with hydrogen cyanide in the presence of ammonia as a base. Even when a base other than ammonia is used in this preparation procedure, the 2-amino-4-(methylthio)butanenitrile still contains ammonia. The reason for this is that the hydrogen cyanide used for preparing 2-amino-4-(methylthio)butanenitrile typically still contains unreacted ammonia, independently whether it was prepared according to the Andrussow process or the BMA process, also referred to as Degussa process. As a consequence, any 2-amino-4-(methylthio)butanenitrile used in a hydrolysis to methionine as well as the hydrolysis intermediate 2-amino-4-(methylthio)butaneamide and the final hydrolysis product methionine always contain ammonia.

However, the presence of ammonia in the methionine comprising mixture inevitably leads to the formation of an ammonium salt of methionine. It is therefore not possible to obtain neutral methionine or ammonia free methionine using the process according to EP 3199519 A1. Rather, the contacting of 2-amino-4-(methylthio)butanenitrile and/or 2-amino-4-(methylthio)butaneamide with water always gives a methionine containing mixture with ammonium methioninate as the main product, and therefore, the thus obtained methionine comprising product must be subjected to crystallization in order to obtain neutral methionine, i.e. methionine free from ammonia. Preferably, the crystallization is performed directly from the aqueous ammonium methioninate comprising aqueous solution obtained from the contacting step. Alternatively, it is also possible to precipitate a methionine comprising product, i.e. containing ammonium methioninate as the main product, from said solution, followed by separation from the solution, dissolving it again in a suitable solvent, preferably in water, and to perform the re-crystallization the thus obtained second solution. In the context of the present invention said second solution is also referred to as a methionine comprising mixture.

In another embodiment the process according to the present invention further comprises the step of crystallizing or re-crystallizing methionine from the methionine comprising mixture obtained from at least one contacting step.

The process according to the present invention therefore preferably comprises the steps of i) a first contacting of a solution or suspension comprising 2-amino-4-(methylthio)butanenitrile and/or 2-amino-4-(methylthio)butaneamide with water in the presence of a catalyst to give a methionine comprising mixture, wherein the catalyst comprises $CeO_2$ comprising particles, wherein the $CeO_2$ comprising particles have a BET surface area of from 175 to 300+/−10% $m^2/g$, preferably 200+/−10% to 280+/−10% $m^2/g$, or 225+/−10% to 265+/−10% $m^2/g$, measured according to DIN ISO 9277-5 (2003), a mean maximum Feret diameter $x_{Fmax,\ mean}$ of from 3+/−10% to 40+/−10% nm, preferably 4+/−10% to 10+/−10% nm and a mean minimum Feret diameter $x_{Fmin,\ mean}$ of from 2+/−10% to 30+/−10% nm, preferably 3+/−10% to 10+/−10% nm, both measured according to DIN ISO 9276-6 (2012), ii) optionally, feeding the methionine comprising mixture obtained from step i) to at least one further contacting step, iii) separating the catalyst from the methionine comprising mixture of step i) and/or step ii) by a continuous cross flow filtration, and iv) crystallizing or re-crystallizing methionine from the methionine comprising mixture obtained from step iii).

In alternative or in addition, the process according to the present invention therefore preferably comprises the steps of i) a first contacting of a solution or suspension comprising 2-amino-4-(methylthio)butanenitrile and/or 2-amino-4-(methylthio)butaneamide with water in the presence of a catalyst to give a methionine comprising mixture, wherein the catalyst comprises $CeO_2$ comprising particles, wherein the $CeO_2$ comprising particles have a BET surface area of from 175 to 300+/−10% $m^2/g$, preferably 200+/−10% to 280+/−10% $m^2/g$, or 225+/−10% to 265+/−10% $m^2/g$, measured according to DIN ISO 9277-5 (2003), a mean maximum Feret diameter $x_{Fmax,\ mean}$ of from 3+/−10% to 40+/−10% nm, preferably 4+/−10% to 10+/−10% nm and a mean minimum Feret diameter $x_{Fmin,\ mean}$ of from 2+/−10% to 30+/−10% nm, preferably 3+/−10% to 10+/−10% nm, both measured according to DIN ISO 9276-6 (2012), ii) optionally, feeding the methionine comprising mixture obtained from step i) to at least one further contacting step, iii) separating the catalyst from the methionine comprising mixture of step i) and/or step ii) by a continuous cross flow filtration, ii') optionally, repeating steps i) and iii), or steps i) to iii), and iv) crystallizing or re-crystallizing methionine from the methionine comprising mixture obtained from the last separation step iii), when the step ii') was performed at least once.

According to the technical teaching of EP 3199519 A1, 2-amino-4-(methylthio)butanenitrile is prepared by contacting 3-(methylthio)propionaldehyde, hydrogen cyanide and ammonia with each other, and therefore the starting material for preparing methionine also contains ammonia. It is therefore not surprising that almost all examples of this document were performed using an aqueous solution of 2-amino-4-(methylthio)butanenitrile, which still contains ammonia. Only the example 5 of that document was performed with a deammoniated 2-amino-4-(methylthio)butanenitrile. In comparison to the other examples, the methionine yield obtained in this example is only 80% and thus, significantly lower than in the other examples of EP 3199519 A1. Based on these results, one should expect that the presence of a base such as ammonia was beneficial for high yields when preparing methionine by hydrolyzing 2-amino-4-(methylthio)butanenitrile. However, it was found that it is also possible to obtain high methionine yields in the hydrolysis from 2-amino-4-(methylthio)-butanenitrile and/or 2-amino-4-(methylthio)butaneamide with a reduced ammonium methioninate formation. It was found that this effect is achieved in that the at least one contacting step of the process according to the present invention is accompanied by a vacuum distillation or a stripping of the reaction solution or suspension with water vapor to remove ammonia at least partially from the reaction solution or suspension. Performing the contacting step of the process according to the present invention under a reduced pressure allows the reaction solution or suspension to relax, which results in a liberation of ammonia from the solution or suspension. By stripping with water vapor, the ammonia contained in the reaction solution or suspension is carried away from said solution or solution and removed from the reaction system.

In yet another embodiment the process according to the present invention the at least one contacting step is accompanied by a vacuum distillation or a stripping of the reaction solution or suspension with water vapor.

The process according to the present invention therefore preferably comprises the steps of i) a first contacting of a solution or suspension comprising 2-amino-4-(methylthio)butanenitrile and/or 2-amino-4-(methylthio)butaneamide with water in the presence of a catalyst to give a methionine comprising mixture, wherein the catalyst comprises $CeO_2$ comprising particles, wherein the $CeO_2$ comprising particles have a BET surface area of from 175 to 300+/−10% $m^2/g$, preferably 200+/−10% to 280+/−10% $m^2/g$, or 225+/−10% to 265+/−10% $m^2/g$, measured according to DIN ISO 9277-5 (2003), a mean maximum Feret diameter $x_{Fmax,\ mean}$ of from 3+/−10% to 40+/−10% nm, preferably 4+/−10% to 10+/−10% nm and a mean minimum Feret diameter $x_{Fmin,\ mean}$ of from 2+/−10% to 30+/−10% nm, preferably 3+/−10% to 10+/−10% nm, both measured according to DIN ISO 9276-6 (2012), ii) optionally, feeding the methionine comprising mixture obtained from step i) to at least one further contacting step, iii) separating the catalyst from the methionine comprising mixture of step i) and/or step ii) by a continuous cross flow filtration, and iv) crystallizing or re-crystallizing methionine from the mixture obtained from step iii), wherein at least one of steps ii) to iv) are accompanied by a vacuum distillation or a stripping of the reaction solution or suspension with water vapor.

In alternative or in addition, the process according to the present invention therefore preferably comprises the steps of i) a first contacting of a solution or suspension comprising 2-amino-4-(methylthio)butanenitrile and/or 2-amino-4-(methylthio)butaneamide with water in the presence of a catalyst to give a methionine comprising mixture, wherein the catalyst comprises $CeO_2$ comprising particles, wherein the $CeO_2$ comprising particles have a BET surface area of from 175 to 300+/−10% $m^2/g$, preferably 200+/−10% to 280+/−10% $m^2/g$, or 225+/−10% to 265+/−10% $m^2/g$ measured according to DIN ISO 9277-5 (2003), a mean maximum Feret diameter $x_{Fmax,\ mean}$ of from 3+/−10% to 40+/−10% nm, preferably 4+/−10% to 10+/−10% nm and a mean minimum Feret diameter $x_{Fmin,\ mean}$ of from 2+/−10% to 30+/−10% nm, preferably 3+/−10% to 10+/−10% nm, both measured according to DIN ISO 9276-6 (2012), ii) optionally, feeding the methionine comprising mixture obtained from step i) to at least one further contacting step, iii) separating the catalyst from the methionine comprising mixture of step i) and/or step ii) by a continuous cross flow filtration, ii') optionally, repeating steps i) and iii), or steps i) to iii), and iv) crystallizing or re-crystallizing methionine from the methionine comprising mixture obtained from the last separation step iii), when the step ii') was performed at least once, wherein at least one of steps ii) to iv) are accompanied by a vacuum distillation or a stripping of the reaction solution or suspension with water vapor.

Preferably, steps ii) and iii), steps ii) and iv), steps iii) and iv), or all of steps ii) to iv), independently if performed once or repeated, are accompanied by a vacuum distillation or a stripping of the reaction solution or suspension with water vapor.

The ammonia thus removed from the reaction solution or suspension can be used in the conversion of 2-hydroxy-4-(methylthio)butanenitrile to give 2-amino-4-(methylthio)butanenitrile in a reaction step upstream to the process according to the present invention.

The catalyst used in the process according to the present invention is not subject to any limitations regarding its preparation, provided that the preparation provides the $CeO_2$ comprising particles comprised in the catalyst with the technical features according to the present invention, in particular with a BET surface area of from 175 to 300+/−10% $m^2/g$, preferably 200+/−10% to 280+/−10% $m^2/g$, 225+/−10% to 265+/−10% $m^2/g$ measured according to DIN ISO 9277-5 (2003), a mean maximum Feret diameter $x_{Fmax,\ mean}$ of from 3+/−10% to 40+/−10% nm, preferably 4+/−10% to 10+/−10% nm and a mean minimum Feret diameter $x_{Fmin,\ mean}$ of from 2+/−10% to 30+/−10% nm, preferably 3+/−10% to 10+/−10% nm, both measured according to DIN ISO 9276-6 (2012). For example, they can be prepared according to example 1 of the published patent application EP 1 506 940.

The present invention is further described by the following figures and examples.

EXAMPLES

1. Analytical Methods 1.1 HPLC-chromatography:

Chromatographic analyses of 2-hydroxy-4-(methylthio)butanenitrile (MMP-CN), 2-amino-4-(methylthio)butanenitrile (MMP-AN), 2-amino-4-(methylthio)butaneamide (Met-amide), 3-(methylthio)propionaldehyde (MMP), and methionine (Met) were performed using HPLC systems from JASCO or Agilent with an RP-18 column (250×4.6 mm; 5 µm) and a subsequent UV detection at 210 nm. As eluent, a mixture consisting of 3.3 g $H_3PO_4$, 6.8 g $CH_3CN$, and 89.9 g $H_2O$ was used with a flow of 1 mL/min. 10 µL of the respective sample solution (50 mg sample in 25 mL $H_2O$) were injected into the eluent for analysis. Calibration was done in advance by injection of suitable standard stock solutions of the analyst and a subsequent comparison of peak areas with external standards as commonly done in organic chemical syntheses.

1.2 BET Surface Area:

The BET surface areas $A_{BET}$ were determined by physical adsorption of nitrogen on the surface of the solid and by calculating the amount of adsorbate gas corresponding to a monomolecular layer on the surface according to the Brunauer, Emmett, and Teller (BET) method. The samples used (0.2-0.9 g) were degassed at 150° C. for 20 min under vacuum prior to the measurement. The determination was then carried out at the temperature of liquid nitrogen (77 K). The amount of gas adsorbed was measured by a static-volumetric, 3-point measurement using a TriStar 3000 Miromertrics instrument. The method is described in general in DIN ISO 9277-5 (2003) and was being applied accordingly.

1.3 X-Ray Powder Diffraction and Degree of Crystallinity:

X-ray powder diffraction (XRPD) is a non-destructive analytical technique for determination of crystalline phases in solid samples. XRPD measurements including the determination of the degree of crystallinity were performed as follows. 0.5-2.0 g of the material were analyzed in the Cubix3 Pharma X-ray powder diffractometer from PANalytical using the following parameters:

X-ray tube: LFF-Cu X-ray tube, Cu Kα, λ=0.1542 nm
Generator settings: 40 mA, 40 KV
Detector: X'Celerator
Rotation: Yes/1 Rev./s
2-Theta Range: 5°-100°
Step (° 2Θ): 0.0170
Time per step: 40 s The results were evaluated by using the current version of the PANalytical HighScore Plus software and up-to-date version of the ICDD database with crystalline reference phases. The crystallinity of the material was determined using the constant background method implemented in the HighScore Plus PANalytical software. This method is based on the following equation:

$$\text{Crystallinity } [\%] = \frac{100 \times A}{A + B - C}$$

wherein
- A is the integral area underneath the crystalline reflections,
- B represents the area of the amorphous background and is the integral area between the crystalline reflections and the instrument background line, and
- C is the integral area below the instrument background line caused by air scattering of X-rays, fluorescence radiation and other instrument factors.

The integral area A was determined in the X-ray diffractograms by laying down the background line, which separates the crystalline reflections from the apparent amorphous background. The instrument background line (constant background) and thus the integral area C was determined by measuring a $CeO_2$ NIST certified reference material with 100% crystallinity. The integral area B is determined in the measured samples by laying down the amorphous background and by applying the constant instrument background determined in the $CeO_2$ NIST certified reference material.

1.4 High-Resolution Transmission Electron Microscopy (HR-TEM):

A Jeol 2010F field emission transmission electron microscope was operated at 200 keV acceleration voltage. The calibration, quality and stability of the system was carried out with the Magical no. 641 standard (Norrox Scientific Ltd., Beaver Pond, Ontario, Canada). High resolution transmission electron microscopy (HR-TEM) was used for determination of the distance between lattice planes. Samples were prepared by manually dispersing 10 mg of a powder in 2 mL of chloroform or 2 mL of a 2:1 mixture of isopropanol/water in a clean test tube. The dispersion was agitated for 3 minutes using a UP100H ultrasonic probe (Hielscher) which was introduced deep into the test tube to 1 cm distance to the bottom. During this time, the test tube was located additionally in a Sonorex Super RK102H ultrasonic bath (Bandelin, 240 W peak energy input). HR-TEM supports coated with holey carbon foil were used as a support (CF200-Cu Carbon film on 200 mesh copper grids; producer: Electron Microscopy Sciences, Hatfield, PA). 10 µL of the dispersion were transferred onto the carbon foil using a Transferpette (Brand).

For spot analyses of the nanoparticles, energy dispersive X-ray nano-spot-analyses (EDX) were performed using a Noran SiLi detector with a 30 mm² crystal and a Noran System Six device.

For statistical evaluation of the maximum Feret diameter $x_{Fmax}$, minimum Feret diameter $x_{Fmin}$, aspect ratio $x_{Fmin}/x_{Fmax}$, projection area A, and equivalent circular diameter $x_A$ of the nanoparticles, 500 particles of a sample were selected manually from a HR-TEM analysis and evaluated according to DIN ISO 9276-6 (2012) using the I-TEM software of Soft Imaging Systems (SIS), Münster, Germany. The obtained values were used for the calculation of the corresponding mean values $x_{Fmax, mean}$, $x_{Fmin, mean}$, $x_{Fmin, mean}/x_{Fmax, mean}$, $A_{mean}$, and $x_{A, mean}$.

2. Preparation of Catalysts According to the Invention

The catalysts according to the present invention are not subject to any limitation regarding their preparation, provided that the procedure used for their preparation gives catalysts with the features according to the present invention. In the present case, the catalysts #1 and #2 according to the present invention were purchased from Treibacher Industrie AG.

The powder of the different catalysts was analyzed for their Brunauer, Emmett, and Teller (BET) surface area $A_{BET}$, degree of crystallinity, and their mean maximum Feret diameter $x_{Fmax, mean}$, minimum Feret diameter $x_{Fmin, mean}$, mean aspect ratio $x_{Fmin, mean}/x_{Fmax, mean}$, lattice plane distance, and mean equivalent circular diameter $x_{A, mean}$ using high resolution transmission electron microscope (HR-TEM) and a subsequent graphical analysis of 500 particles. The catalysts #3 and #4 were purchased from Wako Pure Chemicals Ltd., the catalyst #5 was purchased from Kanto Chemical Co., Inc., and the catalyst #6 was purchased from Daiichi Kigenso Kagaku Kogyo Co., Ltd., respectively, and analyzed for the same parameters as the catalysts according to the present invention.

TABLE 1

Summary of the tested catalysts

| Catalyst # | Catalyst composition | Crystallinity [%] | Lattice plane distance [nm] | $A_{BET}[m^2/g]$ | $x_{A, mean}$ [nm] | $x_{Fmax, mean}$ [nm] | $x_{Fmin, mean}$ [nm] | $x_{Fmin, mean}/x_{Fmax, mean}$ |
|---|---|---|---|---|---|---|---|---|
| #1 | $CeO_2$ | 60 | 0.31 | 232 | 4.1 | 5.0 | 3.7 | 0.74 |
| #2 | $CeO_2$ | 60 | 0.31 | 264 | 4.2 | 5.1 | 3.8 | 0.75 |
| #3[1] | $CeO_2$ | 80 | 0.32-0.40 | 23 | 21.9 | 26.7 | 18.6 | 0.89 |
| #4[1] | $CeO_2$ | 96 | 0.30-0.31 | 3.9 | 48.1 | 59.9 | 41.9 | 0.71 |
| #5[1] | $CeO_2$ | 80 | 0.31 | 57 | 5.7 | 24.6 | 4.7 | 0.23 |
| #6[1] | $CeO_2$ | 59 | 0.28-0.32 | 159.6 | 4.1 | 5.1 | 3.6 | 0.73 |

([1]comparative examples).

3. Synthesis Examples 3.1 Synthesis of 2-amino-4-(methylthio)butanenitrile Starting from 2-hydroxy-4-(methyl-thio)butanenitrile 10.1 g 2-hydroxy-4-(methylthio)butanenitrile (MMP-CN; 90 wt.-% in water, 69.3 mmol, 1 mol.eq.) were mixed with 26.0 g $NH_3$ (32 wt.-% in water, 7 mol.eq., 48.8 mmol) in a glass reactor and sealed subsequently. The slightly beige colored and turbid emulsion containing 25 wt.-% MMP-CN was stirred and heated to 50° C. for 30 minutes by means of a pre-heated water bath. The obtained light yellow solution was analyzed by HPLC chromatography confirming a 100% conversion of MMP-CN with a selectivity of 98.8% towards 2-amino-4-(methylthio)butanenitrile (MMP-AN; 67.2 mmol) and 2-amino-4-(methylthio)butaneamide (Met-amide; 1.2 mmol).

3.2 Direct Conversion of the Obtained 2-amino-4-(methylthio)butanenitrile Towards a mixture comprising 2-amino-4-(methylthio)butaneamide and methionine To the reaction solution obtained according to example 3.1 comprising 8.75 g MMP-AN (67.2 mol), 0.18 g Met-amide (1.2 mmol), 7.14 g NH3 (419 mmol, 6 mol.eq.), and 19.9 g water, another 36.2 g water (MMP-AN concentration 12 wt.-%) and 1.0 g (5.8 mmol, 0.09 mol.eq.) of the $CeO_2$-containing catalysts #1 to #2 of table 2 were added. The glass reactor was again sealed and heated to 60° C. for 30 minutes by means of a pre-heated water bath while the reaction was stirred. Subsequently, the reaction solution was rapidly cooled to room temperature and analyzed by HPLC chromatography. In addition, the reaction was also carried in the presence of $ZrO_2$ (catalyst #7) and without the presence of any catalyst. Results regarding the conversion of MMP-AN, the selectivity towards methionine (Met), the combined selectivity towards Met-amide and Met, the ratio of Met:Met-amide, the yield of Met, and the combined yield of Met-amide and Met are listed in table 2.

TABLE 2

Summary of the results of example 3.2

| Cat. # | Catalyst composition | X [%] MMP-AN | Y [%] Met + Met-amide | Y [%] Met | Ratio Y Met:Met-amide | S [%] Met + Met-amide | S [%] Met |
|---|---|---|---|---|---|---|---|
| #1 | $CeO_2$ | 82 | 80 | 31 | 0.6 | 98 | 38 |
| #2 | $CeO_2$ | 87 | 86 | 37 | 0.7 | 99 | 43 |
| #3[1] | $CeO_2$ | 46 | 28 | 2 | 0.08 | 61 | 4 |
| #4[1] | $CeO_2$ | 33 | 24 | 1 | 0.04 | 73 | 3 |
| #5[1] | $CeO_2$ | 85 | 97 | 17 | 0.3 | 79 | 20 |
| #6[1] | $CeO_2$ | 91 | 82 | 31 | 0.6 | 91 | 34 |
| #7[1] | $ZrO_2$ | 35 | 24 | 2 | 0.07 | 70 | 6 |
| none[1] | — | 18 | 11 | 0 | 0 | 63 | 0 |

([1]comparative examples, X = conversion, Y = yield, S = selectivity)

3.3 Direct Full Conversion of the Obtained 2-amino-4-(methylthio)butanenitrile Towards Methionine The reaction solution obtained according to example 3.1 comprising 8.76 g MMP-AN (67.3 mol), 0.18 g Met-amide (1.2 mmol), 7.14 g $NH_3$ (419 mmol, 6 mol.eq.), and 19.9 g water was transferred to a stainless steel autoclave reactor and another 36.2 g water (MMP-AN concentration 12 wt.-%) and 4.0 g (23 mmol, 0.35 mol.eq.) of the $CeO_2$-containing catalysts #1 to #4 and catalyst #6 according to table 3 were added. The reactor was sealed and heated to 75° C. for 120 minutes by means of an electric block heater while the reaction was stirred. Subsequently, the reaction solution was rapidly cooled to room temperature and analyzed by HPLC chromatography. Results regarding the conversion of MMP-AN, the selectivity towards methionine (Met), the combined selectivity towards Met-amide and Met, the ratio of Met:Met-amide, the yield of Met, and the combined yield of Met-amide and Met are listed in table 3.

TABLE 3

Summary of the results of example 3.3

| Cat. # | Catalyst composition | X [%] MMP-AN | Y [%] Met + Met-amide | Y [%] Met | Ratio Y Met:Met-amide | S [%] Met + Met-amide | S [%] Met |
|---|---|---|---|---|---|---|---|
| #1 | $CeO_2$ | 100 | 100 | 100 | 99 | 100 | 100 |
| #1 + 3 eq. #7 | 25 wt.-% $CeO_2$ 75 wt.-% $ZrO_2$ | 100 | 97 | 95 | 48 | 97 | 95 |
| #3[1] | $CeO_2$ | 100 | 87 | 35 | 0.7 | 87 | 35 |
| #4[1] | $CeO_2$ | 95 | 94 | 31 | 0.5 | 99 | 33 |
| #5[1] | $CeO_2$ | 100 | 86 | 81 | 16 | 86 | 81 |
| #6[1] | $CeO_2$ | 100 | 98 | 98 | —[2] | 98 | 98 |

([1]comparative examples; [2]no Met-amide was detected, X = conversion, Y = yield, S = selectivity)

3.4 Direct Conversion of the Obtained 2-amino-4-(methylthio)butanenitrile Towards a Mixture Comprising 2-amino-4-(methylthio)butaneamide and Methionine at Different Start Concentrations of the Obtained 2-amino-4-(methylthio)butanenitrile To the reaction solution obtained according to example 3.1 comprising 8.75 g MMP-AN (67.2 mol), 0.18 g Met-amide (1.2 mmol), 7.14 g NH3 (419 mmol, 6 mol.eq.), and 19.9 g water, another 0 g, 36.2 g, or 110 g water (MMP-AN concentration 24 wt.-%, 12 wt.-%, or 6 wt.-%) and 0.5 g catalyst #1 according to table 1 (2.9 mmol, 0.04 mol.eq.) were added. The glass reactor was again sealed and heated to 60° C. for 30 minutes by means of a pre-heated water bath while the reaction was stirred. Subsequently, the reaction solution was rapidly cooled to room temperature and analyzed by HPLC chromatography. Results regarding the conversion of MMP-AN, the selectivity towards methionine (Met), the combined selectivity towards Met-amide and Met, the ratio of Met:Met-amide, the yield of Met, and the combined yield of Met-amide and Met are listed in table 4.

TABLE 4

Summary of the results of example 3.4, C = concentration, X = conversion, Y = yield, S = selectivity.

| C [%] MMP-AN | X [%] MMP-AN | Y [%] Met + Met-amide | Y [%] Met | Ratio Y Met:Met-amide | S [%] Met + Met-amide | S [%] Met |
| --- | --- | --- | --- | --- | --- | --- |
| 6 | 95 | 97 | 57 | 1.6 | 97 | 60 |
| 12 | 88 | 97 | 33 | 0.7 | 97 | 34 |
| 24 | 78 | 62 | 20 | 0.5 | 80 | 26 |

3.5 Reacting the Obtained Solution Comprising 2-amino-4-(methylthio)butaneamide and Methionine at Elevated Temperatures for Full Conversion to Methionine The reaction solution obtained according to example 3.2 with catalyst #1 according to table 2 was transferred to a stainless steel autoclave reactor and heated to 120° C. for 120 minutes by means of an electric block heater while the reaction was stirred. Subsequently, the reaction solution was rapidly cooled to room temperature. The solution was analyzed by HPLC chromatography revealing 98% conversion of Met-amide with a selectivity to Met of 91%, which equals to a yield of Met of 91%.

3.6 Separating the Catalyst from a Methionine Comprising Mixture by a Continuous Cross Flow Filtration A methionine comprising mixture comprising 3 wt.-% Met and 1 wt.-% of catalyst #1 according to table 1 was pumped through an $Al_2O_3$ channel (support) covered by a membrane made of $Al_2O_3$ with a membrane pore diameter of 50 nm or covered by a membrane made of $ZrO_2$ with a nominal molecular weight cutoff (NMWC) of 150 or 25 kD. In each of the cases, the permeate was analyzed by HPLC chromatography and revealed a successful and unhindered passing of Met through the membrane with an identical Met concentration of 3% as compared to the starting methionine comprising mixture. In each of the cases, a particle size distribution analysis by laser diffraction as well as dynamic light scattering of the permeate solution revealed that the catalyst was fully retained in the retentate and did not pass the membrane.

The invention claimed is:

1. A process for producing methionine, the process comprising contacting a solution or suspension comprising at least one selected from the group consisting of 2-amino-4-(methylthio)butanenitrile and 2-amino-4-(methylthio)butaneamide with water in the presence of a catalyst to give a methionine comprising mixture, wherein the catalyst comprises $CeO_2$ comprising particles, wherein the $CeO_2$ comprising particles have a BET surface area of 225+/−10% to 300+/−10% m²/g measured according to DIN ISO 9277-5 (2003), a mean maximum Feret diameter $x_{Fmax,\ mean}$ of 3+/−10% to 40+/−10% nm, a mean minimum Feret diameter $x_{Fmin,\ mean}$ of 2+/−10% to 30+/−10% nm, and a mean aspect ratio $x_{Fmin,\ mean}/x_{Fmax,\ mean}$ of 0.55+/−10% to 0.80+/−10%, each measured according to DIN ISO 9276-6 (2012).

2. The process of claim 1, wherein the catalyst comprises 25 to 100 wt.-% $CeO_2$, based on a total weight of the catalyst.

3. The process of claim 1, wherein the $CeO_2$ comprising particles comprise 50 to 100 wt.-% $CeO_2$, based on a total weight of the $CeO_2$ comprising particles.

4. The process of claim 1, wherein the BET surface area of the $CeO_2$ comprising particles is 225+/−10% to 265+/−10% m²/g.

5. The process of claim 1, wherein the $CeO_2$ comprising particles have a lattice plane distance of 0.24+/−10% to 0.32+/−10% nm.

6. The process of claim 1, wherein the $CeO_2$ comprising particles comprise octahedral particles.

7. The process of claim 1, wherein the $CeO_2$ comprising particles have a mean equivalent circular diameter $x_{A,\ mean}$ of 3+/−10% to 30+/−10% nm, measured according to DIN ISO 9276-6 (2012).

8. The process of claim 1, wherein the $CeO_2$ comprising particles have a crystallinity of at least 50%.

9. The process of claim 1, wherein the contacting is performed at a temperature no greater than 90° C. with a 2-amino-4-(methylthio)butanenitrile comprising solution or suspension.

10. The process of claim 1, further comprising contacting the methionine comprising mixture with water in the presence of the catalyst.

11. The process of claim 10, wherein the contacting of the methionine comprising mixture is performed at a temperature of 70 to 140° C.

12. The process of claim 1, further comprising separating the catalyst from the methionine comprising mixture by a continuous cross flow filtration.

13. The process of claim 1, wherein the method further comprises vacuum distilling the methionine comprising mixture or stripping the with water vapor following the contacting.

* * * * *